United States Patent [19]

Torres et al.

[11] Patent Number: 5,219,580
[45] Date of Patent: Jun. 15, 1993

[54] THERMOPLASTIC SILICONE SHAPED ARTICLES FOR CONTROLLED RELEASE OF IODINE VALUES TO DOMESTIC WATER SUPPLIES

[75] Inventors: Ghislaine Torres; Christian Prud'Homme, both of Lyon, France

[73] Assignee: Rhone-Poulenc Chimie, Courbevoie, France

[21] Appl. No.: 535,169

[22] Filed: Jun. 8, 1990

[30] Foreign Application Priority Data

Jun. 8, 1989 [FR] France ............................ 89 07831

[51] Int. Cl.⁵ .............. A01N 59/22; A61K 33/36; C02F 1/68
[52] U.S. Cl. ................... 424/667; 424/668; 424/669; 424/670; 424/671; 424/672; 424/422; 210/753
[58] Field of Search ................ 424/78, 667, 668, 669, 424/670, 671, 672

[56] References Cited

U.S. PATENT DOCUMENTS

| | | | |
|---|---|---|---|
| 2,441,320 | 5/1948 | Hyde | 528/10 |
| 3,279,996 | 10/1966 | Ing, Jr. et al. | 424/424 |
| 3,832,458 | 8/1974 | Merrill | 424/424 |
| 3,854,480 | 12/1974 | Zaffaroni | 424/424 |
| 3,907,720 | 9/1975 | Field et al. | 424/78 |
| 4,352,833 | 10/1982 | Young et al. | 424/78 |
| 4,387,196 | 6/1983 | Bonnet et al. | 528/10 |
| 4,500,337 | 2/1985 | Young et al. | 424/78 |
| 4,814,184 | 3/1989 | Aguadisch et al. | 424/78 |
| 4,871,547 | 10/1989 | Cyprien et al. | 424/78 |
| 4,880,617 | 11/1989 | Chromecek et al. | 424/78 |
| 4,886,661 | 12/1989 | Cyprien et al. | 424/78 |

FOREIGN PATENT DOCUMENTS

| | | |
|---|---|---|
| 0283407 | 9/1988 | European Pat. Off. . |
| 0283408 | 9/1988 | European Pat. Off. . |
| 0284521 | 9/1988 | European Pat. Off. . |
| 2707549 | 8/1978 | Fed. Rep. of Germany . |

Primary Examiner—Thurman K. Page
Assistant Examiner—Peter F. Kulkosky
Attorney, Agent, or Firm—Burns, Doane, Swecker & Mathis

[57] ABSTRACT

Silicone dosage forms adapted for the continuous and controlled release of iodine values, notably to domestic water supplies for the treatment of the various disease states attributed to iodine deficiency, are heat-shaped from (A) a thermoplastic silicone copolymer, and (B) a therapeutically effective amount of at least one water soluble, nontoxic, organic and/or inorganic iodine compound which is in solid state at ambient temperature.

16 Claims, No Drawings

THERMOPLASTIC SILICONE SHAPED ARTICLES FOR CONTROLLED RELEASE OF IODINE VALUES TO DOMESTIC WATER SUPPLIES

CROSS-REFERENCE TO COMPANION PATENTS/APPLICATIONS

U.S. Pat. Nos. 4,871,547 and 4,886,661, and copending applications Ser. Nos. 161,445 and 161,133, filed Feb. 26, 1988, Ser. No. 386,422, filed Jul. 28, 1989 and Ser. No. 386,704, filed Jul. 31, 1989, all assigned to the assignee hereof all now abandoned.

BACKGROUND OF THE INVENTION

1. Field of the Invention

The present invention relates to silicone-based compositions containing an iodine compound, to dosage forms shaped therefrom and adapted for the controlled release of iodine values, and to a process for treating domestic water supplies and beverages utilizing such compositions/dosage forms.

2. Description of the Prior Art

The number of subjects exhibiting a deficiency or an inadequacy of iodine is currently estimated at several hundred million worldwide. The geographical regions affected to the greatest degree are Latin America, particularly along the Andean Cordillera, and virtually all noncoastal countries of Africa and of Asia (Pakistan, India, Nepal, China, Laos, etc.).

The principal pathological consequences of iodine deficiency are well known. These are essentially, on the one hand, goiter and its complications, among which may be included swallowing disorders, respiratory disorders, cancer, peripheral circulation and, on the other hand, hypothyroidism and its complications, among which may be mentioned: cretinism, cerebral disorders, premature births, miscarriages and congenital abnormalities.

While iodine deficiency has disappeared from industrialized countries because, for example, the salts used for cooking are iodized, this is not the case in the developing countries, where the two main campaigns undertaken to date have proven ineffective.

These campaigns have for their focus, on the one hand:

(i) the iodination of cooking salt; this is not effective in the majority of the developing countries because very frequently the consumption of salt is minimal, the systems for the distribution of salt via the economic and commercial networks are virtually nonexistent and, finally, in a tropical region, iodine which is added to salt escapes rapidly if it is not perfectly packaged; and, on the other hand:

(ii) the intramuscular injection of iodinated oil; this injection has the advantage of exhibiting a delayed action, but it is not devoid of disadvantages, particularly the risk of infection, the risk of iodine allergy, and the risks of hyperthyroidism or of hypothyroidism, which are caused by the injection of a necessarily supraphysiological dosage.

SUMMARY OF THE INVENTION

Accordingly, a major object of the present invention is the provision of silicone-based composition containing iodine which, after shaping as desired, are suitable for use in the continuous treatment of water for domestic use, particularly in water supply and treatment systems in wells and boreholes. The subject compositions make it possible to release a controlled and measured amount of iodine with a view to ensuring the collective treatment of the various manifestations due to an iodine deficiency, as well as a prophylaxis of these various manifestations.

Another object of the invention is to provide a silicone composition containing iodine which, after appropriate shaping and suitably immersed in water sources to be treated, especially wells and boreholes, continually releases, preferably for at least one year, an appropriate amount of iodine in a therapeutically active and effective form and dosage in order to treat the various disease states caused by iodine deficiency.

Yet another object of the invention is to provide suitable shaped articles which can easily be introduced and loaded into wells and/or boreholes containing the water source to be treated.

Published French Patent Applications Nos. 2,611,733 and 2,611,734, assigned to the assignee hereof, describe compositions containing, in addition to the iodine compound, at least one polyorganosiloxane in the form of an oil or resin, and a catalyst for producing elastomers from these compositions. Such compositions enable the above objectives to be met. However, the elastomeric shaped articles containing an iodine compound and produced from such compositions present the disadvantage of containing the catalysts required for curing into elastomeric state.

Thus, still another object of the present invention is to provide silicone compositions containing an iodine compound, in which the polymeric matrix does not include undesirable impurities such as, for example, catalysts.

Another object of this invention is to provide compositions which, in addition to the iodine compound, contain only silicone-based polymeric materials.

Yet another object of the present invention is to provide silicone compositions in which the polymeric material can be purified before it is shaped, for example by dissolving it in organic solvents followed by reprecipitation (in a nonsolvent) before being mixed with the iodine compound.

Another object of this invention is to provide silicone compositions in which the polymer employed with the iodine compound is soluble in certain organic solvents.

Another object of this invention is to provide silicone compositions in which the iodine compound can be distributed homogeneously, by stirring, in a solution of the polymer employed.

Another object of this invention is to provide silicone compositions permitting easy production of shaped articles therefrom, by molding or by extrusion, under the influence of temperature.

Another object of the present invention is to provide shaped articles produced from such compositions, these articles, upon being placed in appropriate water source, releasing the iodine compound essentially according to zero-order kinetics and continuously until 80% by weight and more of the iodine compound has been released.

Briefly, the present invention features novel compositions that can be shaped by molding or by extrusion under the action of heat, comprising:

(A) a thermoplastic silicone copolymer, and (B) at least one organic and/or inorganic iodine compound in solid form at room temperature, soluble in water and nontoxic.

The present invention also features novel articles shaped from the above compositions, and to the treatment of potable water utilizing such shaped articles.

DETAILED DESCRIPTION OF THE PREFERRED EMBODIMENTS OF THE INVENTION

More particularly according to the present invention, the thermoplastic silicone copolymers comprising the subject compositions are advantageously block copolymers which are either linear multiblock copolymers, the substantially linear principal polymer chain of which comprises alternating polydiorganosiloxane segments or blocks and organic segments or blocks, or graft copolymers which comprise a polydiorganosiloxane polymer chain onto which organic chains are grafted.

The organic radicals of the diorganosiloxyl units are preferably $C_1$–$C_4$ alkyl radicals, in particular methyl, 3,3,3-trifluoropropyl radicals and phenyl radicals.

In addition, the thermoplastic copolymers which can be used within the scope of the present invention are polymers which soften under the effect of heat, which are soluble in certain organic solvents and the shaping of which entails reversible physical processes.

The preferred thermoplastic copolymers are those which have a Tg (glass transition temperature) or melting point (in the case of semicrystalline polymers) which are higher than room temperature (25° C.) and preferably higher than 40° C., and generally lower than 200° C.

The thermoplastic silicone copolymers employed according to the present invention are advantageously soluble in at least one of the organic solvents, or mixture of organic solvents, selected among chloroform, acetone, methyl ethyl ketone, tetrahydrofuran, dichloroethane, tetrachloroethane, carbon tetrachloride, trichloroethylene, hexane, heptane, methanol, ethanol, isopropanol and toluene.

The organic block segments, blocks or grafts of the thermoplastic silicone copolymers may be, in particular:
(i) Polyurethanes (see, for example, Canadian Patent CA-A-1,072,241, U.S. Pat. Nos. 4,145,508, 4,180,515 and 4,518,758);
(ii) Polysilarylenes (see, for example, U.S. Pat. No. 4,233,427, FR-A-2,407,950 and FR 1,299,160);
(iii) Polystyrenes (see, for example, U.S. Pat. No. 4,263,401);
(iv) Polyesters (see, for example, U.S. Pat. No. 3,701,815);
(v) Polyethers;
(vi) Polycarbonates (see, for example, *J. Polym. Sci., Polymer Letters Ed.* 7 p. 569–577 (1969);
(vii) Polyamides;
(viii) Polyimides;
(ix) Polyimides/amides;
(x) Polysulfones;
(xi) Polyacrylates;
(xii) Polymethacrylates;

and, in general, the thermoplastic silicone copolymers described at pages 181 to 198 of the 1988 edition of *Inorganic and Organometallic Polymers.*

The thermoplastic silicone copolymers according to the present invention can thus be especially those described in the above patents, hereby expressly incorporated by reference.

For example, such copolymers may advantageously be (according to the above U.S. Pat. No. 4,233,427) those which have a plurality of recurring units corresponding to either or both of the following formulae F1 and F'1:

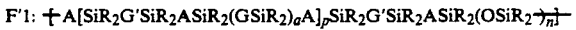

in which the symbols A, which are identical, are linear or branched chain alkylene radicals having from 2 to 6 carbon atoms, or cyclohexylene radicals; the symbols R, which may be identical or different, are each an alkyl or haloalkyl radical having from 1 to 5 carbon atoms, a cycloalkyl or halocycloalkyl radical having from 3 to 8 carbon atoms, an aryl or haloaryl radical having from 6 to 8 carbon atoms, a cyanoalkyl radical having from 3 to 4 carbon atoms; the symbols G, which are identical, are linear or branched chain alkylene radicals having from 1 to 8 carbon atoms, or divalent organic radicals corresponding to the formula $F_2$:

in which the symbols Q, which are identical, are either of the groups —O— and —OCO— (—OCO— being bonded to T via the radical —CO—); the symbol T is a monocyclic, divalent hydrocarbon radical having from 6 to 8 carbon atoms, or a divalent organic radical having from 10 to 22 carbon atoms, comprising 2 hydrocarbon rings fused to each other or linked via a valence bond or by one of the groups of the formulae —O—, —CH2—, —C(CH3)2— and —Si(R')2—, wherein R' is an alkyl radical having from 1 to 3 carbon atoms; the symbols x, which are identical, denote 1, 2 or 3, or a divalent hydrocarbon radical corresponding to the formula $F_3$: $(CH_2)_bT(CH_2)_b$ in which the symbol T is as defined in formula $F_2$ and the symbols b, which are identical, denote 0 or 1; the symbols G', which are identical, are as defined for G, except that they do not correspond to the formula $F_2$; the symbols which are identical, denote 0 or 1; the symbol p denotes any number ranging from 1 to 120; and the symbol n denotes any number ranging from 1 to 1500.

In the compositions according to the present invention, the organic segments, blocks or grafts, are present in a weight amount of 5% to 60%, preferably from 10% to 40% relative to the total weight of the thermoplastic silicone copolymer.

Exemplary inorganic iodine compounds, with the exception of molecular iodine $I_2$, are, whether singly or in admixture:

iodides or iodates of the general formula:

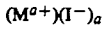

and

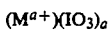

in which a is an integer greater than or equal to 1 and M is a cation selected from among an alkali metal such as sodium and potassium, an alkaline earth metal such as magnesium and calcium, a transition metal such as iron and manganese, and a quaternary ammonium $(NY_4)^+$, in which the radicals Y, which may be identical or different, are each a linear or branched chain $C_1$-$C_{20}$ alkyl radical or a hydrogen atom, such as the ammonium ion $NH_4^+$.

The cations $M^{a+}$ and $NY_4^+$ are selected such that the corresponding iodide or iodate is a solid or a liquid at room temperature, is soluble in water and is nontoxic.

The iodides and iodates which may be employed are advantageously those of the formulae:

NaI; $NaIO_3$;
KI; $KIO_3$;
$MgI_2$; $MgI_2.8H_2O$;
$Mg(IO_3)_2.4H_2O$;
$NH_4I$;
$FeI_2.4H_2O$;
$MnI_2$.

These salts may contain water of hydration or water of formation.

An exemplary compound of iodine, which is at the same time organic and inorganic, is, for example, the calcium iodobehenate of the formula:

$(C_{21}H_{42}ICO_2)_2Ca$

Iodinated polyvinylpyrrolidone is also an exemplary organic iodine compound.

For reasons of ease of use, solid iodine compounds are preferred and, among the latter, NaI and $KIO_3$ are preferred.

All of the iodine compounds as described above release iodine in a nontoxic and therapeutically effective form when they are dissolved in the water to be treated. By "nontoxic iodine compound" according to the invention is intended a compound which, in solution, is not toxic in the dosages recommended consistent herewith.

By "water-soluble iodine compound" is intended a compound which has a solubility of at least 500 mg/l at room temperature.

In general, from 5 to 130 parts (by weight), preferably from 10 to 90 parts, of iodine compound (B) are employed per 100 parts of the thermoplastic silicone copolymer (A) in the composition according to the present invention.

In the developing countries in particular, water for domestic use (drinking, washing, irrigation and the like) is essentially provided by structures of two types, wells and boreholes.

For obvious reasons of cost, efficiency and health, the creation of a new water source is frequently produced by drilling.

A borehole is a column of air drilled through compact rocks which has a depth which generally ranges from 20 to 100 meters and has a diameter of at least approximately 10 cm. Water filters into this column through cracks or various interstices. The water reserve which is immediately available thus constituting 10 to 70 meters, generally from 30 to 50 meters, in height, which is withdrawn, for example, using an immersed-body pump.

This water is principally renewed as a function of the use of the borehole, which depends on the season. In fact, in the rainy season the borehole is traditionally used less. On the other hand, in the dry season, the borehole is operated for approximately 10–12 hours daily, which represents an amount of from 5 to 10 $m^3$ per day for approximately six months.

As a general rule, a well may be run dry twice daily during the dry season, which corresponds to a maximum usage of 5 to 10 $m^3$, based on these average statistical data.

Numerous studies show that in the regions which are highly endemic in goiter, the preexisting proportion of iodine equivalent in the water in boresholes or in wells is less than 2 micrograms per liter (2 $\mu g/l$). It is currently estimated that a daily intake of approximately 100 $\mu g$ of iodine equivalent per day per person would be sufficient to prevent the development of endemic goiter and doubtless approximately 150 $\mu g$ in the presence of regular consumption of giotrogenic substances. Conversely, an acute iodine intoxication may be responsible for neurological irritation, for hyperthyroidism or for hypothyroidism.

It is assumed in the medical arts that the ingestion of a dose of 3 grams of iodine equivalent by an adult subject at a single dose does not produce any secondary effect.

Consequently, the desired objective is to provide an individual with 20 to 200 $\mu g$, preferably approximately 100 $\mu g$, of iodine equivalent daily.

Thus, with the knowledge that, on average, an adult individual ingests 2 liters of water daily and on the basis of the above data (a borehole with an output of 600 l/h), it appears desirable that one liter of treated water should contain approximately 50 $\mu g/l$ of iodine, which corresponds to 50 $\mu g$ of iodine equivalent per liter per person, which requires the silicone elastomer to release 720 mg/d of iodine equivalent, i.e., 270 g of iodine equivalent to be released over one year.

The controlled iodine release system forms part of the matrix systems in which the diffusion of the active ingredient is normally determined by Fick's law, namely, by diffusion kinetics on the order of ½ for only 60% by weight of the active ingredient. Beyond 60% the matrix is exhausted and the diffusion fluxes are greatly reduced. Surprisingly and unexpectedly, it has now been found that the matrix system comprising a thermoplastic silicone copolymer in accordance with the invention releases iodine according to zero-order kinetics, continuously, and thus operates until 80% by weight and more of the iodine compound has been released.

The considerable advantage contributed by the thermoplastic silicone copolymer matrix is, therefore, that it is very easy to extrapolate the continuous diffusion of the active ingredient after a measurement of the amount released over at least one month, because it is known that the diffusion kinetics are of zero order and that at least 80% of the iodine compound will be released according to these kinetics.

In order to provide complete control over the release of the active ingredient, it is advantageous to present the thermoplastic silicone copolymer matrix in the form of elementary modules or articles of various shapes such as cubes, parallelepipeds, cylinders and spheres, the fundamental parameters of which are as follows:

(a) the nature of the iodine compound;
(b) the mean diameter (particle size) g of the particles of the iodine compound in the preferred case where the latter is a solid;

(c) the concentration t of the iodine compound within the matrix;

(d) the surface/volume ratio R of the module.

The nature of the iodine compound and its particle size determine the rate of diffusion v of the active ingredient through the matrix.

The lower the value of g, the slower v is and vice-versa.

The higher the value of t, the greater the flux of active ingredient and vice-versa.

The higher the value of R, the greater the flux of active ingredient and vice-versa.

One skilled in this art, by routine experimentation, can easily and rapidly obtain the required result by extrapolating the theoretical elusion time which will correspond to the actual time of diffusion of the active ingredient.

In the case of NaI and $KIO_3$, which are the preferred iodine compounds, g, t and R advantageously range within the following values:

(i) g ranges from 1 to 500 $\mu$m;

(ii) t ranges from 10 to 100 parts by weight of iodine compound per 100 parts by weight of (A); and (iii) R ranges from 0.5 to 50 in the case of a cylindrical shape.

It is desirable, furthermore, that the iodine compound should be dispersed homogeneously within the matrix.

To attain this objective, the thermoplastic silicone copolymer is dissolved in one of (or a mixture of) the appropriate organic solvents selected from among those indicated above, optionally with heating, and when the dissolution is complete the iodine compound is then added with stirring and is distributed homogeneously in the solution. The organic solvent is then evaporated off and the composition obtained is then shaped by heating. The shaped articles comprising the composition according to the present invention are produced, for example, by molding or by extrusion.

These articles may be optionally produced by heating, for example by molding or by extrusion, after the composition has been directly prepared by kneading the finely divided thermoplastic silicone copolymer with the solid iodine compound in powder form, until a homogeneous mixture is obtained. It is then unnecessary to dissolve the thermoplastic silicone copolymer.

EXAMPLE 1

1(1) Preparation of the Thermoplastic Silicone Copolymer

A thermoplastic polyblock copolymer, the preparation of which is described in Example 4 of U.S. Pat. No. 4,233,427 was employed, the $\alpha$, $\omega$-dihydropolydimethylsiloxane used having a number-average molecular weight of 22,800 g/mole, determined by quantitative analysis of the SiH functional groups.

This copolymer was constituted of an alternation of polydimethylsiloxane segments and of poly[(dimethylsilylene)phenylene-(dimethylsilylene)-1,2-ethanediyl)] segments corresponding to the average general formula:

The proportion of polydimethylsiloxane segments in this copolymer was 80% by weight.

the inherent viscosity of this copolymer was 0.44 dl/g (measured at 25° C. in a chloroform solution at a concentration of 3 g/dl).

1(2) Preparation of a Composition According to the Present Invention Comprising the Copolymer Prepared as above 100 g of the copolymer were dissolved in 70 g of anhydrous toluene at a temperature of approximately 110° C.

When the mixture was homogeneous, 25 g of NaI, having a particle size of less than 50 $\mu$m (microns) were added.

The mixture was stirred for 30 min such as to disperse the NaI (insoluble in toluene) homogeneously in the copolymer.

The toluene was then removed in the oven for 5 hours.

1(3) Preparation of an Article by Shaping the above Composition

The composition prepared in 1(2) was then introduced into a 2.3-cm diameter tube and placed in the oven. The temperature was then increased to 210° C. (softening temperature of the copolymer) and maintained thereat for 2 hours.

1(4) Experimental Protocol for Measuring the Elution Kinetics

The shaped article prepared above was cut to the desired length (50 mm), in accordance with the surface/volume ratio (2.14 $cm^{-1}$) which it was desired to provide, and was immersed in a container of 600 ml of distilled water, thermostated at 20° C.

The container was equipped with a magnetic stirring system driven in a slow rotary motion (100 rev/min) ensuring the homogeneity of the solution. It was covered with a lid in order to reduce water evaporation to a minimum.

1-ml samples were withdrawn daily during the initial period of elution, and weekly after a two-week elution.

The concentration of iodide or iodate, released daily, was determined by measurement using an iodine-specific electrode.

Two milliliters of a solution ($K_2SO_4$+ascorbic acid) were added to one milliliter of sample from the container—this solution served as an ion buffer and as a reducing solution in the case where iodates were being measured—together with one milliliter of distilled water. The electrode was immersed in this solution and the electrochemical potential of the solution was monitored. A calibration curve established beforehand using iodine solutions containing $5 \times 10^{-5}$ Ml (M:mole) to $5 \times 10^{-2}$ M/l enabled the iodide or iodate concentration (C) to be calculated in mg/l of the solution.

The characteristics of the immersed cylinder (of the article employed to carry out this measurement) were:

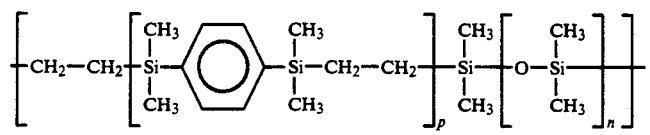

| | |
|---|---|
| Diameter = | 23 mm |
| Height = | 50 mm |
| Surface area = | 44.4 cm² |
| Volume = | 20.76 cm³ |
| S/V = | 2.14 cm⁻¹ |
| Total mass = | 23.17 g |
| Initial quantity of I (Qo) = | 3.92 g. |

The results of the elution kinetics are reported in the following Table 1.

Cumulative Q corresponds to the quantity of I⁻ equivalent (designated the "active ion") eluted at time t.

Given that 80 mol % of the active ion incorporated was eluted in accordance with zero-order kinetics over time, the theoretical elution time (Te) for each example according to the following formula was determined:

$$Te = \frac{0.8 \times Qo}{\text{daily flow}} \quad (Te \text{ being expressed in days})$$

TABLE 1

| Time (day) | Cumulative Q (mgI⁻) | 100 × Q/Qo (%) |
|---|---|---|
| 0.4 | 72 | 1.79 |
| 1 | 77 | 1.92 |
| 2 | 66 | 1.70 |
| 3 | 144 | 3.6 |
| 6 | 187 | 4.7 |
| 7 | 243 | 6.25 |
| 9 | 254 | 6.53 |
| 16 | 315 | 7.97 |
| 23 | 453 | 11.52 |

Te = 150 days

EXAMPLE 2

2(1) The copolymer prepared above in 1(1) was employed.

2(2) A composition was prepared in the same manner, using the same amounts of materials as in 1(2), except that the sodium iodide (NaI) employed had a particle size ranging from 100 to 200 μm (microns).

2(3) This composition was shaped (by molding) to produce an article, in the same manner as in 1(3).

2(4) The elution kinetics were measured (according to 1(4) of iodine compound from the article prepared above and cut to the desired length (50 mm) in accordance with the surface/volume ratio (2.14 cm⁻¹) which it was desired to obtain.

| | |
|---|---|
| Diameter = | 23 mm |
| Height = | 50 mm |
| Surface area = | 44.4 cm² |
| Volume = | 20.76 cm³ |
| S/V = | 2.14 cm⁻¹ |
| Total mass = | 22.5 g |
| Initial quantity of I (Qo) = | 3.81 g. |

The results of the elution kinetics are reported in Table 2 below.

TABLE 2

| Time (day) | Cumulative Q (mgI⁻) | 100 × Q/Qo (%) |
|---|---|---|
| 0.4 | 149 | 3.88 |
| 1 | 259.5 | 6.76 |
| 2 | 381 | 9.99 |
| 3 | 375 | 9.90 |
| 6 | 513.5 | 13.51 |
| 7 | 530 | 13.92 |
| 9 | 579.8 | 15.18 |
| 16 | 728.8 | 19.16 |
| 23 | 1049 | 27.48 |

Te = 80 days

EXAMPLE 3

3(1) The copolymer prepared in 1(1) was employed.

3(2) A composition was prepared in the same manner, using the same amounts of materials as in 1(2), except that the sodium iodide had a particle size ranging from 200 to 400 μm (microns).

3(3) An article was prepared by shaping the composition by molding, as in 1(3).

3(4) The elution kinetics were measured (according to the protocol described in 1(4) of the article (cylinder) prepared in 3(3) and cut to the desired length (50 mm) in accordance with the surface/volume ratio (2.14 cm⁻¹) sought to be produced.

| | |
|---|---|
| Diameter = | 23 mm |
| Height = | 50 mm |
| Surface area = | 44.4 cm² |
| Volume = | 20.76 cm³ |
| S/V = | 2.14 cm⁻¹ |
| Total mass = | 23.04 g |
| Initial quantity of I (Qo) = | 3.9 g. |

The results of the elution kinetics are reported in Table 3 below.

TABLE 3

| Time (day) | Cumulative Q (mgI⁻) | 100 × Q/Qo (%) |
|---|---|---|
| 0.4 | 132.5 | 3.4 |
| 1 | 149 | 3.79 |
| 2 | 303.7 | .83 |
| 3 | 386.5 | 9.84 |
| 6 | 519 | 13.36 |
| 7 | 519 | 13.25 |
| 9 | 646 | 16.51 |
| 16 | 833.7 | 21.38 |
| 23 | 1225.8 | 31.46 |

Te = 58 days

EXAMPLE 4

4(1) The copolymer prepared in 1(1) was employed.

4(2) A composition was prepared in the same manner as in 1(2), but all amounts of the materials employed were divided by two, the sodium iodide being replaced by potassium iodate having a particle size below 50 μm (microns).

4(3) An article was prepared in the same manner as in 1(3), but the tube employed had a diameter of 10 mm.

4(4) The elution kinetics were measured (according to the protocol described in 1(4) of iodine compound from the article (cylinder) prepared in 4(3) and cut to the desired length (20 mm) in accordance with the surface/volume ratio (4.7 cm⁻¹) sought to be obtained.

| | |
|---|---|
| Diameter = | 10.8 mm |
| Height = | 20.5 mm |
| Surface area = | 8.6 cm² |
| Volume = | 1.83 cm³ |
| S/V = | 4.7 cm⁻¹ |

-continued

| | |
|---|---|
| Total mass = | 2.062 g |
| Initial quantity of I (Qo) = | 0.245 g |

The results of the elution kinetics are reported in Table 4 below.

TABLE 4

| Time (day) | Cumulative Q (mgI$^-$) | 100 × Q/Qo (%) |
|---|---|---|
| 1 | 2.91 | 1.19 |
| 2 | 3.85 | 1.57 |
| 3 | 3.82 | 1.56 |
| 6 | 4.72 | 1.93 |
| 7 | 5.63 | 2.30 |
| 9 | 6.52 | 2.66 |
| 16 | 6.44 | 2.63 |
| 23 | 9.14 | 3.73 |

Te = 768 days

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heat-shapable silicone composition for the controlled release of iodine values, comprising (A) a thermoplastic silicone copolymer, and (B) a therapeutically effective amount of at least one water soluble, nontoxic, organic and/or inorganic iodine compound which is in solid state at ambient temperature and which is homogeneously distributed throughout said thermoplastic silicone copolymer (A), said composition not including a catalyst.

2. The silicone composition as defined by claim 1, said thermoplastic silicone copolymer (A) comprising a block copolymer which comprises either a linear multiblock copolymer, the principal polymer chain of which is substantially linear and which comprises alternating polydiorganosiloxane segments or blocks and organic segments or blocks, or a graft copolymer which comprises a polydiorganosiloxane backbone onto which organic chains are grafted.

3. The silicone composition as defined by claim 2, said thermoplastic silicone copolymer (A) comprising a polyurethane, polysilarylene, polystyrene, polyester, polyether, polycarbonate, polyamide, polyimide, polyimides/amide, polysulfone, polyacrylate or polymethacrylate.

4. The silicone composition as defined by claim 3, wherein the amount by weight of the organic sequences, blocks or grafts ranges from 5% to 60%.

5. The silicone composition as defined by claim 1, said thermoplastic silicone copolymer (A) having a glass transition temperature or a melting point higher than 40 C.

6. The silicone composition as defined by claim 1, said thermoplastic silicone copolymer (A) comprising a plurality of recurring units having either or both of the following formulae F1 and F'1:

F1: 

F'1: 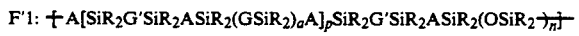

in which the symbols A, which are identical, are each a linear or branched chain alkylene radical having from 2 to 6 carbon atoms, or a cyclohexylene radical; the symbols R, which may be identical or different, are each an alkyl or haloalkyl radical having from 1 to 5 carbon atoms, a cycloalkyl or halocycloalkyl radical having from 3 to 8 carbon atoms, an aryl or haloaryl radical having from 6 to 8 carbon atoms, or a cyanoalkyl radical having from 3 to 4 carbon atoms; the symbols G, which are identical, are each a linear or branched chain alkylene radical having from 1 to 8 carbon atoms, a divalent organic radical having the formula F2:

F2: 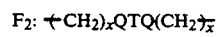

in which the symbols Q, which are identical, are each —O— or —OCO—, with the proviso that the —OCO— radical is bonded to T via the radical —CO—, the symbol T is a monocyclic, divalent hydrocarbon radical having from 6 to 8 carbon atoms, or a divalent organic radical having from 10 to 22 carbon atoms and comprising two hydrocarbon rings fused to each other or joined by a valence bond or by one of —O—, —CH$_2$—, —C(CH$_3$)$_2$— or —Si(R')$_2$—, wherein R' is an alkyl radical having from 1 to 3 carbon atoms, and the symbols, which are identical, are each 1, 2 or 3; or a divalent hydrocarbon radical having the formula F$_3$:

F$_3$: 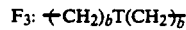

in which the symbol T is as defined in formula F$_2$ and the symbols b, which are identical, are each 0 or 1; the symbols G', which are identical, have the definition of G, with the proviso that they do not correspond to the formula F$_2$; the symbols a, which are identical, are each 0 or 1; the symbol p is a number ranging from 1 to 120; and the symbol n is a number ranging from 1 to 1500.

7. The silicone composition as defined by claim 6, said thermoplastic silicone copolymer (A) comprising a plurality of recurring units of the formula:

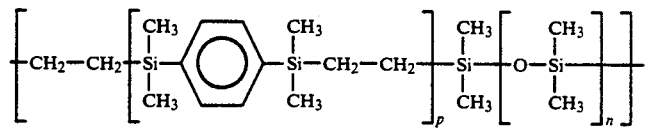

8. The silicone composition as defined by claim 1, comprising from 5 to 130 parts by weight of said at least one iodine compound (B) per 100 parts by weight of said thermoplastic silicone copolymer (A).

9. Silicone composition as defined by claim 1, said at least one iodine compound (B) comprising an iodide or iodate of the general formulae:

$$(M^{a+})(I^-)_a$$

and $$(M^{a+})(IO_3^-)_a$$

in which a is an integer greater than or equal to 1 and M is an alkali or alkaline earth metal, a transition metal, or a quaternary ammonium $(NY_4)^+$ cation, in which latter the radicals Y, which may be identical or different, are each a linear or branched chain $C_1$-$C_{20}$ alkyl radical or a hydrogen atom.

10. The silicone composition as defined by claim 1, said at least one iodine compound (B) comprising NaI, $NaIO_3$, KI, $KIO_3$, $MgI_2$, $MgI_2.8H_2O$, $Mg(IO_3)_2.4H_2O$, $NH_4I$, $FeI_2.4H_2O$ or $MnI_2$.

11. The silicone composition as defined by claim 1, said at least one iodine compound (B) comprising calcium iodobehenate.

12. The silicone composition as defined by claim 1, said at least one iodine compound (B) comprising iodinated polyvinylpyrrolidone.

13. The silicone composition as defined by claim 8, comprising from 10 to 90 parts by weight of said at least one iodine compound (B) per 100 parts by weight of said thermoplastic silicone copolymer (A).

14. A shaped article comprising the silicone composition as defined by claim 1.

15. The shaped article as defined by claim 14, adapted to controlledly and continuously release about 50 μg of iodine equivalent per liter, to an external aqueous environment.

16. In a process for the iodination of a domestic water supply by immersing an iodine-releasing controlled delivery dosage form therein, the improvement which comprises utilizing as the dosage form therefor, the shaped article as defined by claim 14.

* * * * *